(12) United States Patent
Dornbush et al.

(10) Patent No.: US 9,149,682 B2
(45) Date of Patent: Oct. 6, 2015

(54) SYSTEM AND METHOD FOR SHARING OF ATHLETIC PERFORMANCE DATA

(75) Inventors: Sandor Dornbush, Mountain View, CA (US); Rodrigo Damazio, Belo Horizonte (BR); Nicholas Julian Pelly, San Francisco, CA (US); Eduardo Cordeiro, Belo Horizonte (BR)

(73) Assignee: Google Inc., Mountain View, CA (US)

( * ) Notice: Subject to any disclaimer, the term of this patent is extended or adjusted under 35 U.S.C. 154(b) by 131 days.

(21) Appl. No.: 13/540,947

(22) Filed: Jul. 3, 2012

(65) Prior Publication Data

US 2015/0154403 A1    Jun. 4, 2015

Related U.S. Application Data

(60) Provisional application No. 61/504,452, filed on Jul. 5, 2011.

(51) Int. Cl.
*A63B 24/00* (2006.01)
*A63B 71/06* (2006.01)

(52) U.S. Cl.
CPC ............ *A63B 24/0062* (2013.01); *A63B 71/06* (2013.01); *A63B 2024/0025* (2013.01); *A63B 2024/0065* (2013.01)

(58) Field of Classification Search
USPC .......... 463/6, 36, 39, 40, 42; 482/1, 8, 9, 148, 482/901–902
See application file for complete search history.

(56) References Cited

U.S. PATENT DOCUMENTS

| 6,441,846 | B1* | 8/2002 | Carlbom et al. ............. 348/169 |
| 8,200,323 | B2* | 6/2012 | DiBenedetto et al. ......... 600/519 |
| 8,504,718 | B2* | 8/2013 | Wang et al. ................... 709/238 |
| 2002/0188959 | A1* | 12/2002 | Piotrowski ..................... 725/112 |
| 2008/0126476 | A1* | 5/2008 | Nicholas et al. .............. 709/203 |
| 2010/0198453 | A1 | 8/2010 | Dorogusker et al. |
| 2010/0292600 | A1* | 11/2010 | DiBenedetto et al. ......... 600/520 |
| 2011/0271007 | A1* | 11/2011 | Wang et al. ................... 709/238 |

(Continued)

OTHER PUBLICATIONS

"Strava—From the Beginning" Cycling Tips [online]. Feb. 27, 2012. [Retrieved Jun. 17, 2013] Retrieved from the Internet: <cyclingtips.com.au/2012/02/strava-from-the-beginning/>, 11 pages.

(Continued)

*Primary Examiner* — Bach Hoang
(74) *Attorney, Agent, or Firm* — Lerner, David, Littenberg, Krumholz & Mentlik, LLP

(57) ABSTRACT

A system and method for sharing athletic performance data are described herein. The system and method provide the upload of athletic performance data to a publish/subscribe infrastructure. Sensors coupled to a mobile device track various athletic performance metrics. The mobile device transmits this sensor data to an upload server in the form of athletic performance data. The upload server makes the athletic performance available via a publish/subscribe infrastructure. The publish/subscribe infrastructure allows data servers to subscribe to particular data feeds associated with sets of athletic performance data. The data servers receive the athletic performance data via the data feeds to which they are subscribed, and host the athletic performance data. This data may thus be presented to users in a variety of formats, such as by displaying competitors in an event on a map along with the heart rate, cadence, and other performance indicators.

20 Claims, 5 Drawing Sheets

(56) References Cited

U.S. PATENT DOCUMENTS

| | | | |
|---|---|---|---|
| 2012/0047223 A1* | 2/2012 | Tarkoma | 709/217 |
| 2012/0251079 A1* | 10/2012 | Meschter et al. | 386/278 |

OTHER PUBLICATIONS

Rosie, "What is Strava?" Strava Customer Support [online]. Sep. 6, 2011. [Retrieved Jun. 17, 2013]. Retrieved from the Internet: <https://strava.zendesk.com/entries/20420137-What-is-Strava->, 2 pages.

"Strava—How It Works" Strava.com [online]. © 2013. [Retrieved Jun. 17, 2013]. Retrieved from the Internet: <www.strava.com/how-it-works>, 5 pages.

Jack Purcher, "Apple Introduces us to the Smart Bike" Patently Apple [online]. Aug. 5, 2010. [Retrieved Jun. 17, 2013]. Retrieved from the Internet: <www.patentlyapple.com/patently-apple/2010/08/apple-introduces-us-to-the-bike.html>, 12 pages.

"Athlosoft MOBILE Version 1.3 released" athlosoft®—Solutions for Athletes [online]. Arpil 23, 2010. [Retrieved Jun. 17, 2013]. Retrieved from the Internet: <www.athlosoft.com/?p=2126>, 3 pages.

"Hands on review of the Sony Ericsson Xperia Active ANT+ enabled waterproof phone" DC Rainmaker [online]. Sep. 12, 2011. [Retrieved Jun. 17, 2013]. Retrieved from the Internet: <www.dcrainmaker.com/2011/09/hands-on-review-of-sony-ericsson-xperia.html>, 28 pages.

"Sports Tracker" Wikipedia [online]. Last modified Apr. 25, 2013. [Retrieved Jun. 17, 2013] Retrieved from the Internet: <en.wikipedia.org/wiki/Sports_Tracker>, 1 page.

"Introducing Sports Tracker" Sports-Tracker.com [online]. © 2010-2011. [Retrieved Jun. 17, 2013]. Retrieved from the Internet: <www.sports-tracker.com/blog/about/>, 2 pages.

* cited by examiner

SYSTEM AND METHOD FOR SHARING OF ATHLETIC PERFORMANCE DATA

CROSS-REFERENCE TO RELATED APPLICATIONS

The present application claims the benefit of the filing date of U.S. Provisional Patent Application No. 61/504,452 filed Jul. 5, 2011, the disclosure of which is hereby incorporated herein by reference.

BACKGROUND

Widespread availability of high-speed Internet access has provided users with unprecedented access to information. Real-time news feeds and streaming video are now available on many websites, further increasing the user's access to live data. The ubiquity of social media and networks also allows users to share their day-to-day experiences more than ever before. Photos, videos, and other forms of media allow users to connect with one another from across great distances.

Although users are increasingly connected via traditional forms of media such as photos, videos, and instant messages, it is not feasible to simulate the experience of physical proximity, such as taking a walk together, or competing with one another in an event. Sensor data relating to users physical characteristics, such as athletic performance, is not easily sharable or available in real-time. To compare such performance data, users must typically manually transfer athletic performance data to another user, such as via e-mail, physical transfer of a flash drive, or manually upload the data to a web page.

BRIEF SUMMARY

A system and method for sharing athletic performance data are described. Some aspects of the disclosure provide a system for receiving raw sensor data from one or more sensors, converting the raw sensor data to athletic performance data, and uploading that athletic performance data to an upload server. The upload server stores the athletic performance data in a database and publishes the athletic performance data via a publish/subscribe infrastructure. One or more data servers may register for the athletic performance data via the publish/subscribe infrastructure to receive the performance data as it is updated. Aspects may provide the ability for users to access the athletic performance data in real-time. Some uses of this data include viewing real-time athlete performance data (e.g., heart rate, energy output, and velocity of competitors in a marathon or bike race), and receiving performance data for comparison purposes (e.g., comparing the user's athletic performance data with a friend's performance data as the user jogs around a standard length track).

DETAILED DESCRIPTION

Figure 1:
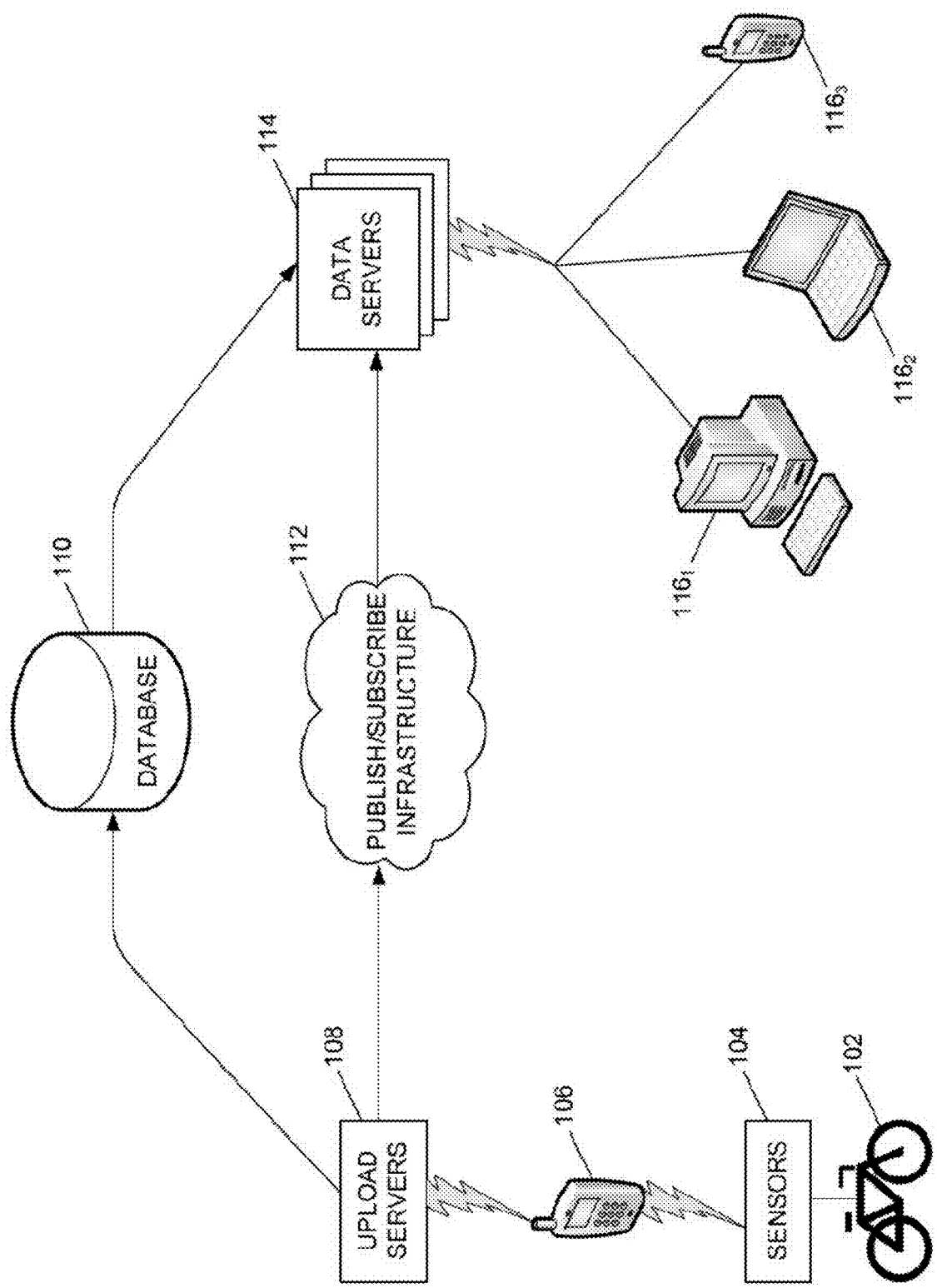
FIG. 1 is a system diagram depicting an example of a system for sharing athletic performance data in accordance with aspects of the disclosure.

Embodiments of a system and method for sharing athletic performance data are described herein. Aspects of the disclosure provide an efficient method for sharing athletic performance data in real-time. Performance data, such as velocity, heart rate, location, power output, and other athletic data may be received by a client device from one or more sensors. The client device may format and upload the performance data to an upload server. The upload server may store the athletic performance data in a database and publish the performance data to one or more data servers via a publish/subscribe infrastructure.

The term "publish/subscribe" generally refers to a messaging pattern whereby senders (publishers) of data, such as an upload server, do not program data messages to be sent directly to specific receivers, such as data servers. Rather, messages are characterized into classes without knowledge of what, if any, subscribers there may be. Subscribers express interest in one or more classes, and only receive messages that are of interest, without knowledge of what, if any, publishers there are. This decoupling of publishers and subscribers can allow for greater scalability and a more dynamic network topology. Publish/subscribe infrastructures may be provided in a decentralized manner, such as via a peer-to-peer system. The use of a publish/subscribe infrastructure provides a scalable, fault-tolerant system for distributing athletic performance data to a large number of users. As such, a relatively small number of upload servers may provide data to millions of users without overloading system resources.

The data servers may reformat, process, and/or display the data to users. For example, users may track the performance of athletes competing in an event in real-time via a web page hosted on the data server. Other exemplary uses may include using the data for comparison to a user athletic performance and providing the data in real-time with a video broadcast of a sporting event.

For situations in which the systems discussed here collect information about users, the users may be provided with an opportunity to opt in/out of programs or features that may collect personal information (e.g., information about a user's location, a user's preferences or a user's contributions to social content providers). In addition, in some examples, certain data may be anonymized in one or more ways before it is stored or used, so that personally identifiable information is removed. For example, a user's identity and location may be anonymized so that the personally identifiable information cannot be determined or associated for the user and so that identified user preferences or user interactions are generalized (for example, generalized based on user demographics) rather than associated with a particular user. Aspects that rely on a user location may identify the location in a general manner. For example, the system may provide information in a binary manner (e.g., a user is nearby, or they are not nearby) rather than specifically identifying a proximity or location.

FIG. 1 is a system diagram depicting an exemplary system 100 for sharing athletic performance data in accordance with aspects of the disclosure. The system 100 receives sensor data via one or more sensors 104, converts the raw sensor data to athletic performance data, and uploads the athletic performance data via a mobile device 106 in communication with an upload server 108. The upload server 108 may reformat and transmit the athletic performance data to a publish/subscribe infrastructure 112 and a database 110. One or more data servers 114 may register with the publish/subscribe infrastructure to receive the athletic performance data in real-time. The data servers 114 may use this performance data for a variety of purposes, including transmission to client devices 116.

The sensors 104 track the performance of an athlete. For example, the sensors 104 may monitor the heart rate, power output, and velocity of the athlete as he pedals on the bicycle 102. The sensors 104 may include devices that are attached to or integrated within the bicycle 102, or they may be separate sensors such as a heart rate monitor worn by the athlete. Although elements of the exemplary system are described with respect to a bicyclist, it should be appreciated that the same or similar sensors could be used for a variety of activities, including but not limited to jogging, walking, running, swimming, and various team and solo sports such as football, baseball, basketball, tennis, and the like.

The sensors 104 may communicate with a mobile device 106. The client device 106 may interact with the sensors 104 via a wired or wireless link, using a network protocol such as Bluetooth, ANT+, 802.11, or any other wired or wireless communication method. The performance data transmitted from the sensors 104 to the client device 106 may be in a native protocol or format associated with each sensor 104. The client device 106 may aggregate and format the performance data into a common format for transmission to an upload server 108. In some aspects, the mobile device 106 executes an application that handles the communication with the sensors 104. For example, a user may download a performance monitoring application that, when executed on the mobile device, allows for configuration, receipt, and transmission of performance data.

The mobile device 106 may convert the sensor data into a format suitable for transmission to the upload server 108. This sensor data may be formatted into a set of athletic performance data. The upload server 108 receives the athletic performance data and manages distribution and processing of the performance data. The mobile device 106 may transmit the performance data in real-time via various network protocols, such as 3G, Long-term Evolution (LTE), WiMax, or any other network protocol. The upload server 108 may store received data in memory, such as via a database 110. The upload server 108 may also manage the transmission of performance data using the publish/subscribe infrastructure 112.

The data server(s) 114 accesses the performance data published by the upload server 108. The data server 114 may provide a variety of functions using the performance data. For example, the data server 114 may provide the performance data in real-time to one or more client devices 116. The performance data may be displayed along with other content, such as a video of the athletic performance or a map overlay. The data servers 114 may also transmit the data directly to the client devices 116 for use in an athletic performance monitoring application. For example, a user may track their personal athletic performance compared to the performance data received from the data servers 114. The data servers 114 may also interface with the database 110 to receive past performance data. For example, the data server may retrieve past information from the database after registering with the publish/subscribe infrastructure, but prior to receiving athletic performance data from the publish/subscribe infrastructure, ensuring that the data server 114 has access to archived data that will not be newly transmitted via the publish/subscribe infrastructure 112.

The publish/subscribe infrastructure 112, and the intervening nodes between the upload server 108 and the data server 114, may comprise various configurations and use various protocols including the Internet, World Wide Web, intranets, virtual private networks, local Ethernet networks, private networks using communication protocols proprietary to one or more companies, cellular and wireless networks (e.g., Wi-Fi), instant messaging, hypertext transfer protocol ("HTTP") and simple mail transfer protocol ("SMTP"), and various combinations of the foregoing. Although only a few devices are depicted in FIG. 1, it should be appreciated that a typical system may include a large number of connected computers. Aspects of the system may use other methods of network communication, such as a "browser channel" or "hanging GET." These techniques allow a HTTP connection to be left open indefinitely, with new data streamed from the server as it becomes available.

Although certain advantages are obtained when information is transmitted or received as noted above, other aspects of the system and method are not limited to any particular manner of transmission of information. For example, in some aspects, information may be sent via a medium such as an optical disk or portable drive. In other aspects, the information may be transmitted in a non-electronic format and manually entered into the system.

Although some functions are indicated as taking place on the mobile device 106, the upload server 108, and/or the data server 114, various aspects may be implemented by a single computer having a single processor. In accordance with one aspect of the system and method, operations performed on the mobile device 106, the upload server 108, and/or the data server 114 may be implemented at other nodes of the network, and vice-versa.

Figure 2:
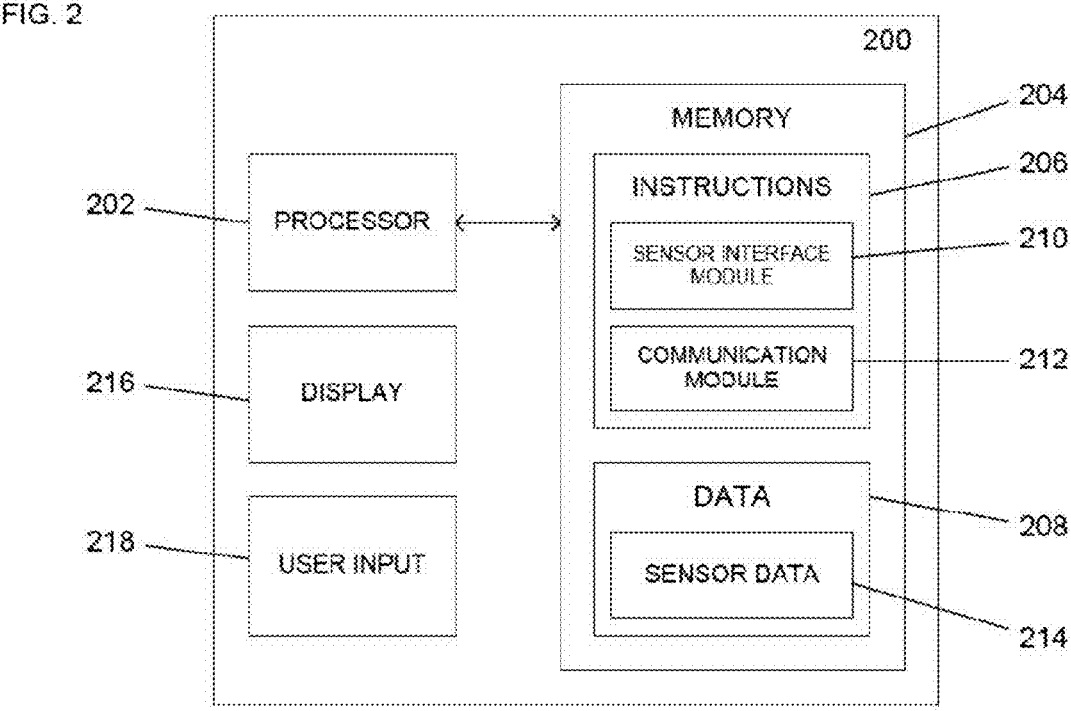
FIG. 2 is a block diagram depicting an example of a mobile device for tracking and uploading athletic performance data in accordance with aspects of the disclosure.

FIG. 2 is a block diagram depicting an example of a mobile device 200 for tracking and uploading athletic performance data in accordance with aspects of the disclosure. The mobile device 200 may be any device capable of receiving data from one or more sensors 104 that track athletic performance. Such devices may include cellular phones, Personal Digital Assistants, smartphones, tablet computers, netbooks, purpose-built electronic devices for transmitting performance data, and the like. The mobile device 200 may include a processor 202, memory 204 and other components typically present in general purpose computers. The processor 202 may be any processor capable of execution of computer code. Alternatively, the processor may be a dedicated controller such as an application-specific integrated circuit ("ASIC"), field-programmable gate array ("FPGA"), complex programmable logic device ("CPLD"), or other processing device.

The mobile device 200 may have a display 216 comprising a monitor having a screen, a projector, a television, a computer printer, a touch-screen, or any other device that is operable to display information. The mobile device 200 may accept user input via other components 218 such as a mouse, a keyboard, a touch-screen or a microphone. Indeed, devices in accordance with the systems and methods described herein may comprise any device operative to process instructions and transmit data to and from humans and other computers including general purpose computers, network computers lacking local storage capability, etc. The mobile device 200 may also have other components normally used in connection with a wireless mobile device such as a camera, a speaker, a network interface component, and all of the components used for connecting these elements to one another. Some or all of these components may all be internally stored within the same housing, e.g. a housing defined by a plastic shell and LCD screen.

Memory 204 may store information that is accessible by the processor 202, including instructions 206 that may be executed by the processor 202, and data 208. The memory 204 may be of any type of memory operative to store information accessible by the processor 202, including a computer-readable medium, or other medium that stores data that may be read with the aid of an electronic device, such as a hard-drive, memory card, read-only memory ("ROM"), random access memory ("RAM"), digital versatile disc ("DVD") or other optical disks, as well as other write-capable and read-only memories. The system and method may include different combinations of the foregoing, whereby different portions of the instructions and data are stored on different types of media.

The instructions 206 may be any set of instructions to be executed directly (such as machine code) or indirectly (such as scripts) by the processor 202. For example, the instructions 206 may be stored as computer code on the computer-readable medium. In that regard, the terms "instructions," "programs," and "applications" may be used interchangeably herein. The instructions 206 may be stored in object code format for direct processing by the processor 202, bytecode, or in any other computer language including scripts or collections of independent source code modules that are interpreted on demand or compiled in advance.

In some aspects, the instructions 206 may comprise a sensor interface module 210. The sensor interface module 210 communicates to one or more athletic performance sensors, such as the sensors 104 described above (see FIG. 1). These sensors may be integrated into athletic performance equipment (e.g., built into a bicycle), attached to a user (e.g., a heart rate monitor), or integrated with the client device (e.g., a GPS receiver). These sensors 104 communicate with the sensor interface module 210 to store a set of sensor data 214. In some aspects, the sensor interface module 210 may also function as a device driver module for the sensors 104. The sensor interface module 210 processes the sensor data 214 and converts the sensor data 214 into a format suitable for transmission to an upload server. Data in this format may be referred to as athletic performance data. Communications between the mobile device 200 and the sensors 104 may be provided in a variety of manners and protocols, including various wired and wireless protocols such as ANT+, Bluetooth, and the like. Although the present example describes data conversion being performed using the mobile device 200, any part of the system (e.g., the data server, the upload server or the mobile device) may choose to simplify the data. For example, line smoothing algorithms may be executed to give a smoother path and remove GPS imprecision, or the raw number of sensor readings may be reduced (e.g. the sensor data includes a new heart rate every 250 ms, but the data is converted to use the average of the last few such readings instead of all of them).

The instructions 206 may also comprise a communications module 212. The communications module 212 may manage formatting and transmission of the athletic performance data to an upload server, such as the upload server 108 described above (see FIG. 1). The communications module 212 may convert the athletic performance data into one or more data packets suitable for transmission via a network protocol, such as Transmission Control Protocol/Internet Protocol (TCP/IP), or another network protocol. In some aspects, the mobile device 200 is a cellular phone, a smartphone, or a tablet computer and the communication module 212 communicates via 3G, LTE, WiMax, EDGE, or the like to transmit data to the upload server.

The communications module 212 may transmit athletic performance data to the upload server at regular intervals. In some aspects, if the communications module 212 cannot transmit the athletic performance data to the upload server, the athletic performance data is stored on the mobile device 200 until the mobile device 200 can successfully transmit the data. For example, if a user is bicycling through a tunnel, they may not have wireless reception to transmit data. The mobile device 200 might store such data until the user has reception and the device can "phone home" properly.

Although the example described herein describes the sensor interface module 210 and the communications module 212 as two distinct modules, aspects of the disclosure may also provide similar functionality in a single module, or multiple modules. Aspects of the instructions 206 may be implemented as software executing on the processor 202 or by various hardware interfaces, such as ASICs, field-programmable gate arrays ("FPGAs"), etc.

Data 208 may be retrieved, stored or modified by the processor 202 in accordance with the instructions 206. For instance, although the architecture is not limited by any particular data structure, the data may be stored in computer registers, in a relational database as a table having a plurality of different fields and records, Extensible Markup Language ("XML") documents or flat files. The data may also be formatted in any computer readable format such as, but not limited to, binary values or Unicode. By further way of example only, image data may be stored as bitmaps comprised of grids of pixels that are stored in accordance with formats that are compressed or uncompressed, lossless (e.g., BMP) or lossy (e.g., JPEG), and bitmap or vector-based (e.g., SVG), as well as computer instructions for drawing graphics. The data may comprise any information sufficient to identify the relevant information, such as numbers, descriptive text, proprietary codes, references to data stored in other areas of the same memory or different memories (including other network locations) or information that is used by a function to calculate the relevant data.

Portions of the data 208 may comprise the sensor data 214. The sensor data 214 may be stored on the mobile device 200 for conversion to athletic performance data and transmission to the upload server 108 and for later review by a user of the mobile device 200.

Although FIG. 2 functionally illustrates the processor 202 and memory 204 as being within the same block, the processor 202 and memory 204 may actually comprise multiple processors and memories that may or may not be stored within the same physical housing. Accordingly, references to a processor, computer or memory will be understood to include references to a collection of processors, computers or memories that may or may not operate in parallel.

Figure 3:
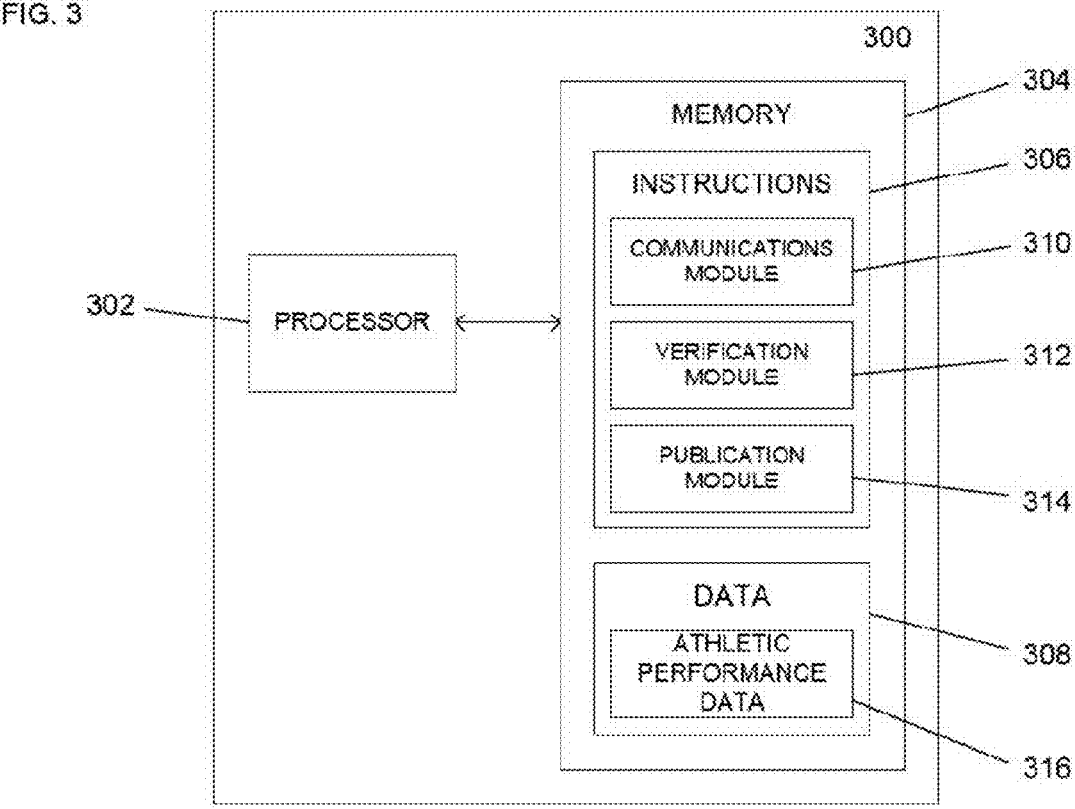
FIG. 3 is a block diagram depicting an example of an upload server for sharing athletic performance data in accordance with aspects of the disclosure.

FIG. 3 is a block diagram depicting an example of an upload server 300 for sharing athletic performance data in accordance with aspects of the disclosure. The upload server 300 functions to receive athletic performance data from one or more mobile devices, such as the mobile device 200. The upload server 300 formats the received athletic performance data, stores the data in a database, such as the database 110, and publishes the athletic performance data via a network. The upload server 300 may be at one node of the network, such as the publish/subscribe infrastructure 112, and be operative to directly and indirectly communicate with other nodes of the network. For example, the upload server 300 may comprise a web server that is operative to communicate with the mobile device 106, a database 110, and one or more data servers 114. The upload server 300 may also comprise a plurality of computers that exchange information with different nodes of a network for the purpose of receiving, processing and transmitting data to the nodes of the network.

The upload server 300 may be configured similarly to the mobile device 200, with a processor 302 and memory 304. As described with respect to the mobile device 200, the memory 304 may comprise a set of instructions 306 and a set of data 308. The processor 302 executes the instructions 306 to control operation of the upload server 300. Athletic performance data 316 received from the mobile device 200 is stored in the data 308. In some aspects, the upload server 300 may wirelessly exchange data with the mobile device 200 over a network such as the Internet. The instructions 306 may include a communications module 310, a verification module 312, and a publication module 314. The communications module 310 communicates with the mobile device 300 to receive athletic performance data.

The verification module 312 verifies the performance data. For example, the verification module 312 may verify a cryptographic signature (e.g., a hash-based message authentication code ("HMAC")) sent by the mobile device 300 along with the athletic performance data. The verification module may compare this cryptographic signature with a signature associated with a user account to verify that the athletic performance data was sent from an authorized user. The verification module 312 may use other methods of data verification. For example, the verification module 312 may prompt the user to log in to a user account, and associate particular accounts (using cookies, for example) with specific mobile devices. Other alternatives may include the use of verification systems such as OAuth/OAuth 2.0, shared-secret encryption, asymmetric-key encryption, and the like.

The publication module 314 publishes the athletic performance data via a publish/subscribe infrastructure. For example, the publish/subscribe infrastructure 112 may comprise a distributed architecture such that nodes may subscribe to updates about specific data. When source nodes, such as the upload server 300, publish athletic performance data for which other nodes have registered, the publish/subscribe infrastructure notifies the subscribing nodes of the new data. In some aspects, the publication module 314 may also manage subscription requests from the data servers 114 to allow the data servers to request certain types of published athletic performance data. The publication module 314 may also store received athletic performance data in a database, such as the database 110 described above (see FIG. 1). In some aspects, the database 110 may be part of the upload server 300, providing an archive of previously received data.

Figure 4:
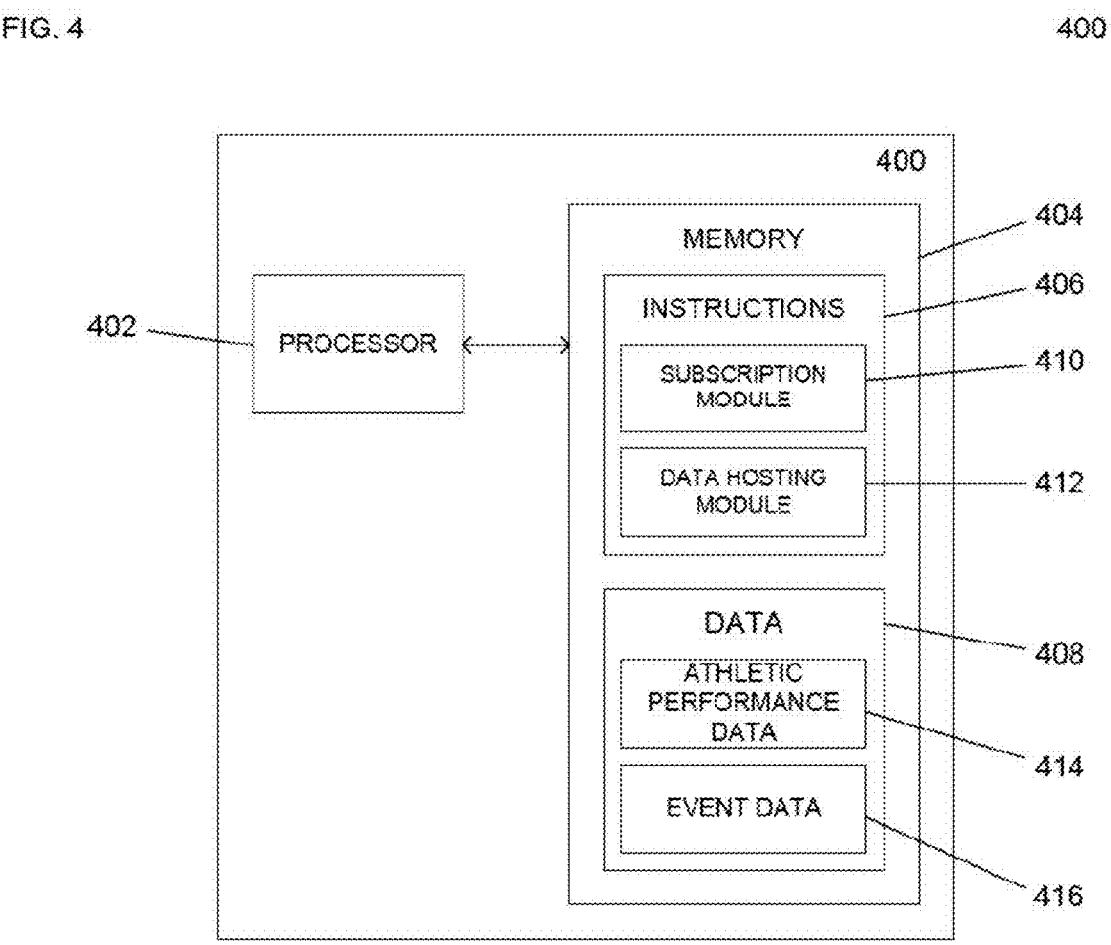
FIG. 4 is a block diagram depicting an example of a data server for sharing athletic performance data in accordance with aspects of the disclosure.

FIG. 4 is a block diagram depicting an example of a data server 400 for sharing athletic performance data in accordance with aspects of the disclosure. The data server 400 performs various operations on athletic performance data received via a publish/subscribe infrastructure. For example, the data server 400 may host a web page displaying athletic performance data of one or more competitors in a competition, or the data server 400 may transmit the athletic performance data to one or more client devices, such as the client devices 116 (see FIG. 1).

The data server 400 may be configured similarly to the mobile device 200 and the upload server 300, with a processor 402 and memory 404. As described with respect to the mobile device 200 and the upload server 300, the memory 404 may comprise a set of instructions 406 and a set of data 408. The processor 402 executes the instructions 406 to control operation of the data server 400. Athletic performance data 414 received via a network, such as the publish/subscribe infrastructure 112, is stored as part of the data 408. The data server 400 may wirelessly exchange data with the upload server 300 and one or more client devices 116 over a network such as the Internet. The instructions 306 may include a subscription module 410 and a data hosting module 412.

The subscription module 410 manages subscriptions to one or more data feeds containing the athletic performance data 414. The subscription module 410 may register the data server 114 with a publish/subscribe infrastructure, such as the publish/subscribe infrastructure 112, and receive the athletic performance data 414 via this network.

The data hosting module 412 may perform various operations on the athletic performance data 414. For example, the data hosting module 412 may function as a web server application to provide the athletic performance data 414 via a web page.

The data hosting module 412 may combine the athletic performance data 414 with various other data to generate output content. For example, the data hosting module 412 may insert the athletic performance data into a streaming video transmission as a video overlay. This combined video may be transmitted to one or more client devices 116. As another example, the data server 114 may store a set of event data 416. The event data 416 may define, for example, one or more legs of a race and the competitors that participate in the event. The athletic performance data 414 may thus be combined with the event data 416 to provide the client devices 116 with a representation of a location and status of each competitor in the event.

The data server 400 may also function to allow a user to access specific performance data for another user. For example, a user may wish to compete in a "virtual race" with a friend. The user might request their friend's athletic performance data for a particular track from the data server 400. The data server 400 may then provide the athletic performance data associated with the user's friend so that the requesting user can compare his or her performance on the track with that of his or her friend.

Figure 5:
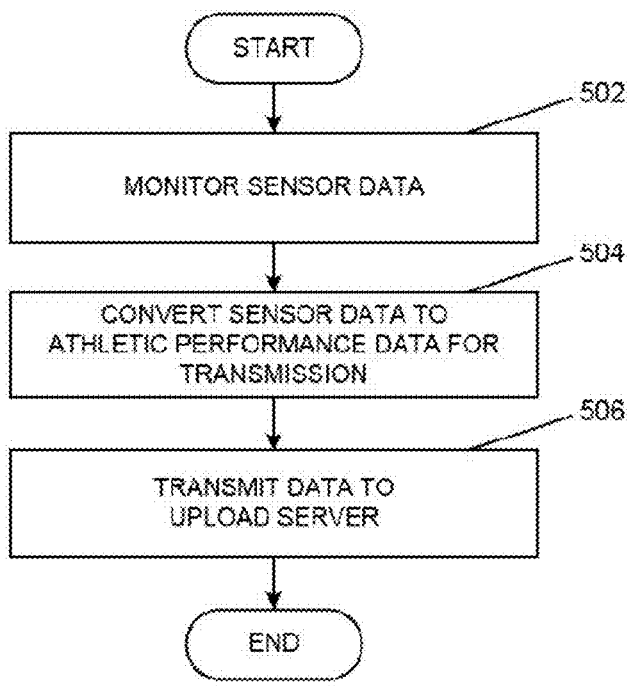
FIG. 5 is a flow diagram depicting an example of a method for providing athletic performance data using a client device in accordance with aspects of the disclosure.

FIG. 5 is a flow diagram depicting an example of a method 500 for providing athletic performance data using a client device in accordance with aspects of the disclosure. The method 500 is operable to convert raw data received from one or more performance sensors into a format suitable for transmission to an upload server. For example, different sensors may use different, proprietary data transmission protocols. The mobile device aggregates and converts this data into a format that can be transmitted to an upload server.

At stage 502, the mobile device monitors sensor data received from one or more performance sensors. For example, a bicyclist may have sensors monitoring his heart rate, power output, velocity, location, pedaling cadence, and the like. Each of these sensors generates data that is monitored by the client device. One example of a protocol by which such sensors may transmit data is the ANT+ protocol, commonly used to transmit data from sensors associated with cycling.

At stage 504, the sensor data received at stage 502 is converted into a format suitable for transmission to the upload server. The mobile device may aggregate multiple sensor data feeds into a single data structure suitable for encoding in a packet for transmission. The converted form of the data may include information identifying a particular user or user account, along with athletic performance data derived from the sensor data. The converted data may also include a cryptographic signature associated with the particular user. This cryptographic signature may be used in conjunction with a cryptographic key held by the upload server to verify the identity of the mobile device that performed the upload operation. In the event other authentication measures are used, the converted data may include an encrypted user identifier or other method of verifying the validity of the data.

At stage 506, the converted data is transmitted to an upload server, such as by a wireless network. As described above, data transmission may occur periodically. If the mobile device is unable to communicate with the upload server, data may be archived locally until communications are reestablished.

Figure 6:
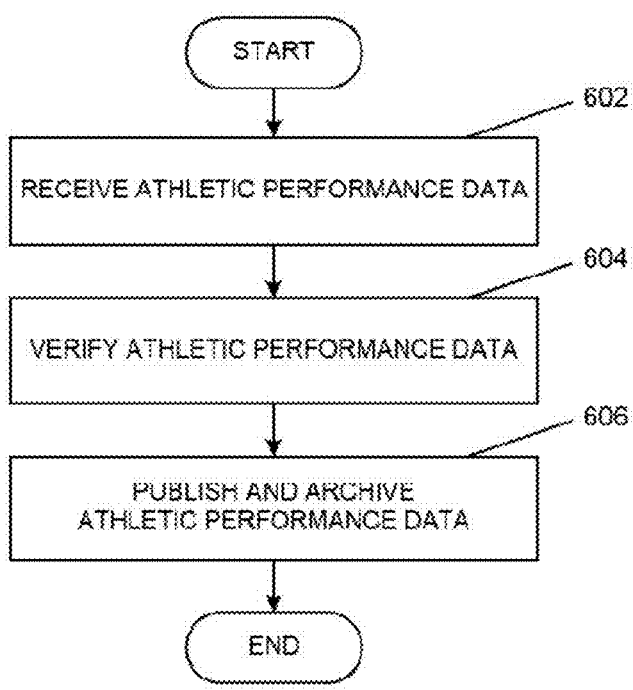
FIG. 6 is a flow diagram depicting an example of a method for processing athletic performance data using an upload server in accordance with aspects of the disclosure.

FIG. 6 is a flow diagram depicting an example of a method 600 for processing athletic performance data using an upload server in accordance with aspects of the disclosure. The method 600 functions to enable a mobile device to receive athletic performance data from one or more mobile devices. The mobile device verifies the data and stores and publishes the data in a manner that allows data servers that have subscribed for the data access to the athletic performance data in real-time.

At stage 602, athletic performance data associated with a particular mobile device is received. The act of receiving the athletic performance data may include storing the data locally on the upload server. The upload server may parse the data to determine with which mobile device the performance data is associated.

At stage 604, the athletic performance data is verified. This verification process may be performed by extracting a cryptographic signature from the athletic performance data, and comparing the cryptographic signature to a unique cryptographic key associated with a particular user. If the key and the signature match, then the data may be identified as valid. If the signature does not match the key, then the data may be discarded.

At stage 606, the athletic performance data is stored in a database and published via a publish/subscribe infrastructure. Once the athletic performance data is stored and published in this manner, any data server that registers for updates regarding performance data associated with the particular mobile device that uploaded the data may access that athletic performance data.

Figure 7:
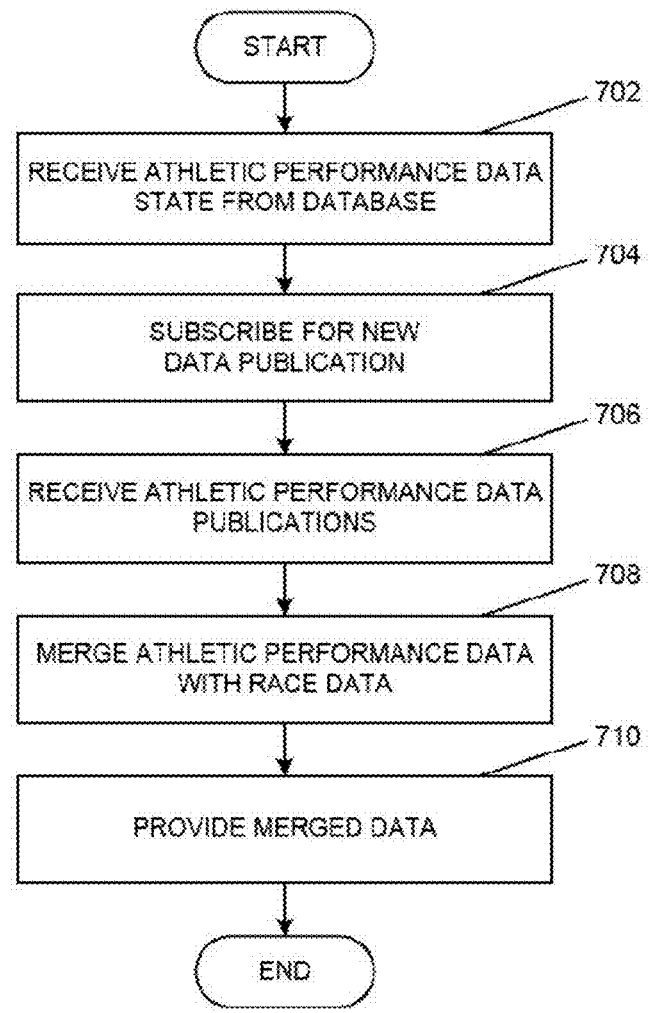
FIG. 7 is a flow diagram depicting an example of a method for accessing published athletic performance data using a data server in accordance with aspects of the disclosure.

FIG. 7 is a flow diagram depicting an example of a method 700 for accessing published athletic performance data using a data server in accordance with aspects of the disclosure. The method 700 is operable to allow a data server to initialize a set of athletic performance data and register for updates to that performance data. The data server may provide that data to client devices in a variety of formats. One particular exemplary method of providing the athletic performance data is described, wherein the athletic performance data is merged with a set of event data to provide users of the client devices with accurate performance information for competitors in an event.

At stage 702, the data server retrieves an initial state of athletic performance data from a database, such as the database 110. The act of retrieving the initial state may also include registering with the publish/subscribe infrastructure. By accessing previous athletic performance data from the database, the data server can determine recent events without the need to request such data via the publish/subscribe infrastructure. Thus the data server is provided with an up-to-date version of events with which to update with data received via the publish/subscribe infrastructure. Loading from a database in this manner results in a more fault-tolerant system, as other data servers may still retrieve the most recent athletic performance data in the event of a data server failure.

At stage 704, the data server subscribes to athletic performance data via the publish/subscribe infrastructure. For example, a data server may request messages associated with a particular user, a particular event, or a particular league. The act of subscribing to a particular data feed ensures that the data server will receive data relating to the feed to which it is subscribed.

At stage 706, athletic performance data for the feed to which the data server has subscribed is obtained. This data may be received via direct message from a node of the publish/subscribe infrastructure. As described above, the publish/subscribe infrastructure provides a scalable method of receiving real-time data.

At stage 708, the athletic performance data is prepared for hosting. In one example, the athletic performance data may be combined with a set of data describing a race (e.g., a map of the route, the identities of the competitors, a video feed of the event) to provide real-time data of the status of the competitors in the event. Such data may be used to supplement a variety of media such as videos, radio reports, web pages, or any other format where a user may which to be informed of athlete performance metrics such as heart rate, power output, pedal cadence, velocity, location, and the like. Other possible uses of the athletic performance data include archiving for later review, or transmission to client devices to allow a user to enter a "virtual race" with a competitor.

At stage 710, the data that was prepared at stage 708 is provided to one or more client devices. Said data is provided in a format appropriate for the data format. For example, web pages may be published on the Internet, merged video feeds may be broadcast as streaming video, virtual races may be transmitted to software applications designed to track user performances in such events, and the like.

The stages of the illustrated methods described above are not intended to be limiting. The functionality of the methods may exist in a fewer or greater number of stages than what is shown and, even with the depicted methods, the particular order of events may be different from what is shown in the figures and include additional stages or omit stages as shown.

The systems and methods described above advantageously provide a scalable method of accessing athletic performance data. The use of a publish/subscribe infrastructure makes the system more resilient than a system that relies on direct data transmissions. Data servers may register for particular data feeds that are relevant to the services that they provide, which enables users to access real-time athletic performance data. Because this data is transmitted in real-time, users do not need to wait for regularly scheduled updates, and a large number of users accessing a particular data server would only interfere with the performance of that particular data server without affecting the rest of the system. The use of a publish/subscribe infrastructure advantageously provides a scalable, fault-tolerant system for distributing athletic performance data to a large number of users. As such, a relatively small number of upload servers may provide data to millions of users without overloading system resources.

As these and other variations and combinations of the features discussed above can be utilized without departing from the disclosure as defined by the claims, the foregoing description of the embodiments should be taken by way of illustration rather than by way of limitation of the disclosure as defined by the claims. It will also be understood that the provision of examples of the disclosure (as well as clauses phrased as "such as," "e.g.", "including" and the like) should not be interpreted as limiting the disclosure to the specific examples; rather, the examples are intended to illustrate only some of many possible embodiments.

The invention claimed is:

1. A computer-implemented method for sharing athletic performance data, comprising:
receiving, using one or more processors, first athletic performance data from a first mobile device during a first user's athletic performance, the athletic performance data comprising sensor data received from one or more athletic performance sensors coupled to the first mobile device;
receiving, using one or more processors, second athletic performance data from a second mobile device during a second user's athletic performance, the athletic performance data comprising sensor data received from one or more athletic performance sensors coupled to the second mobile device;
designating, using the one or more processors, the first athletic performance data into at least one class without knowledge of any subscribe servers subscribed thereto, the subscribe servers subscribing to the at least one class to receive the athletic performance data without knowledge of any publish servers publishing thereof, such that the athletic performance data is compatible with each subscribe server;
publishing, using the one or more processors, the first athletic performance data only to the at least one designated class such that the athletic performance data is transmitted to the subscribe servers of the at least one designated class; and
combining, using the one or more processors and for display to the second user in real-time with the first user's and second user's athletic performance, the first athletic performance data, the second athletic performance data, and a video feed of the first user's athletic performance.

2. The method of claim 1, further comprising storing the first athletic performance data in a database, the database being accessible to the at least one data server.

3. The method of claim 1, wherein the sensor data comprises at least one of: a user heart rate, a user power output, and a user pedal cadence.

4. The method of claim 1, further comprising verifying the first athletic performance data by comparing a first cryptographic signature received with the athletic performance data with a second cryptographic signature associated with a particular user.

5. A processing system for sharing athletic performance data comprising:
at least one processor;
memory, coupled to the at least one processor, for storing a first set of athletic performance data received from a first mobile device during a first user's athletic performance and instructions executable by the processor, and for storing a second set of athletic performance data received from a second mobile device during a second user's athletic performance, the athletic performance data comprising sensor data received from one or more athletic performance sensors coupled to the mobile device;
the processor being configured to:
receive the athletic performance data from the mobile device;
designate the first athletic performance data into at least one class without knowledge of any subscribe servers subscribed thereto, the subscribe servers subscribing to the class to receive the athletic performance data without knowledge of any publish server publishing thereof, such that the athletic performance data is compatible with each subscribe server;
publish the first athletic performance data only to the at least one designated class such that the athletic performance data is transmitted to the subscribe servers of the designated class; and
combine for display to the second user, in real-time with the first user's and second user's athletic performance, the first athletic performance data, the second athletic performance data, and a video feed of the first user's athletic performance.

6. The processing system of claim 5, wherein the processor is further configured to store the first athletic performance data in a database for access by the one or more data servers.

7. The processing system of claim 5, wherein the instructions further comprise a verification module configured to verify the first athletic performance data using a cryptographic key.

8. The processing system of claim 5, wherein the sensor data comprises at least one of: a heart rate, a power output, and a pedal cadence.

9. The processing system of claim 5, wherein the instructions comprise a publication module, the publication module, when executed by the processor, is configured to notify the at least one data server and the subscribe servers thereof of new data.

10. The processing system of claim 5, wherein the instructions comprise a publication module, the publication module, when executed by the processor, is configured to manage a plurality of subscription requests from the subscribe servers.

11. The processing system of claim 5, wherein the instructions further comprise a publication module, the publication module, when executed by the processor, is configured to store the first athletic performance data in a database for later access.

12. The method of claim 1, wherein the publish/subscribe infrastructure notifies the at least one data server and the subscribe servers thereof of new data.

13. The method of claim 1, further comprises managing a plurality of subscription requests from the subscribe servers.

14. The method of claim 1, further comprises storing the first athletic performance data in a database for later access.

15. The method of claim 1, further comprising providing for display to the second user the location of the first user.

16. The method of claim 1, further comprising receiving third athletic performance data from a third mobile device during a third user's athletic performance, wherein the first user's the third user's athletic performance occur at the same sporting event, and wherein said video feed includes the third user's athletic performance.

17. The method of claim 16, wherein the first and third athletic performance data is provided as a video overlay of a streaming video transmission of the sporting event over the Internet.

18. The processing system of claim 5, wherein the processor is further configured to provide for display to the second user the location of the first user.

19. The processing system of claim 5, wherein the processor is further configured to receive third athletic performance data from a third mobile device during a third user's athletic performance, wherein the first user's the third user's athletic performance occur at the same sporting event, and wherein said video feed includes the third user's athletic performance.

20. The processing system of claim 19, wherein the first and third athletic performance data is provided as a video overlay of a streaming video transmission of the sporting event over the Internet.

\* \* \* \* \*